US00RE36374E

United States Patent [19]

Bogeso et al.

[11] E Patent Number: Re. 36,374

[45] **Reissued Date of Patent: *Nov. 2, 1999**

[54] 1,2,3-TRIAZOLE AND TETRAZOLE SUBSTITUTED PIPERIDINE OR TETRAHYDROPYRIDINE COMPOUNDS USEFUL AS ACETYLCHOLINE AGONISTS

[75] Inventors: Klaus Peter Bogeso, Horsholm; Klaus Gundertofte, Frederiksberg; Ejner Knud Moltzen, Gentofte; Henrik Pedersen, Bronshoj, all of Denmark

[73] Assignee: H. Lundbeck, A/S, Copenhagen-Valby, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/648,240

[22] Filed: May 13, 1996

Related U.S. Patent Documents

Reissue of:

[64] Patent No.: 4,866,077
Issued: Sep. 12, 1989
Appl. No.: 07/209,994
Filed: Jun. 22, 1988

[30] Foreign Application Priority Data

Jun. 24, 1987 [GB] United Kingdom ..... 8714789

[51] Int. Cl.[6] ..... A61K 31/445; C07D 401/04

[52] U.S. Cl. ..... 514/326; 514/340; 546/210; 546/276

[58] Field of Search ..... 546/210, 276; 514/326, 340

[56] References Cited

U.S. PATENT DOCUMENTS

| | | | |
|---|---|---|---|
| 4,112,101 | 9/1978 | Sellstedt et al. | 514/340 |
| 4,769,379 | 9/1988 | Katoh et al. | 514/340 |

OTHER PUBLICATIONS

Flood et al. :memory retention test perfomance in Mice: improvement by chronic oral cholinergic drug treatment CA 101:83883, 1984.

Stevenson T "Drug therapy in the management of Parkinson'sdisease" Mediline 09080873, 1997.

Larsson et al. "In vitro binding of 3H–acetylcholine . . . " CA 107:71323, 1987.

Appel, S.H. "Current Neurology" vol. 6, pp. 313–317, 1987.

Marx, J. "Human brain disease recreated in mice" Science, vol. 250, pp. 1509–1510, 1990.

Brain Web News, Press Release, "Lundbeck to proceed at full speed with preparations for the company's public listing—Sales of Cipramil increased by 26% in first half of 1998", Valby, Aug. 19, 1998, 2 pages.

Brain Web Press Cuttings, "Forest Laboratories' Licensed M1 Agonist Not Effective in Alzheimer's Disease", PRNewswire, Aug. 19, 1998, 1 page.

*Primary Examiner*—Ceila Chang
*Attorney, Agent, or Firm*—Darby & Darby

[57] ABSTRACT

The present invention relates to novel compounds of the following formula, where the dotted line designates in optional bond:

I

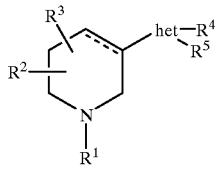

wherein

"het" designates a five membered heterocyclic ring which may include 1 or 2 double bonds and 1–4 heteroatoms selected from nitrogen, oxygen or sulphur, provided that "het" may not designate a 1,4- or 1,3,4-oxadiazole, $R^1$ is selected from hydrogen, lower alkyl, optionally substituted with phenyl which may be substituted with halogen, lower alkyl, or lower alkoxy, or a group $R^6$—CO—NH—$CH_2$— or $R^6$—O—CO—, wherein $R^6$ is lower alkyl, branched or unbranched, or phenyl optionally substituted with halogen, trifuoromethyl, lower alkyl, hydroxy, lower alkoxy, or lower acyloxy;

$R^2$ and $R^3$ are the same or different, each representing hydrogen, lower alkyl, cycloalkyl (3–6 C-atoms), lower alkenyl, lower alkadienyl, lower alkynyl, optionally substituted with hydroxy, halogen or phenyl, in which the phenyl group may be substituted with halogen, trifluoromethyl, lower alkyl, hydroxy or lower alkoxy; $R^2$ and $R^3$ may further, respectively, be selected from trifluoromethyl or phenyl optionally substituted with halogen, trifluoromethyl, lower alkyl, hydroxy, lower alkoxy or lower acyloxy, or $R^2$ and $R^3$ may, respectively, be a group $OR^7$ or $SR^7$ wherein $R^7$ is defined as $R^2$ or $R^3$, and if "het" includes 2 or more carbon atoms $R^4$ and $R^5$ are the same or different, and each is defined as $R^2$ or $R^3$, and if "het" includes only one carbon atom, there is only one substituent, $R^4$, on the heterocyclic ring, and $R^4$ is defined as $R^2$ or $R^3$, as well as individual stereo isomers and pharmaceutically acceptable acid addition salts thereof.

The invention moreover relates to methods for the preparation of the compounds of formula 1, to novel intermediates, to pharmaceutical compositions containing same and to methods for the treatment of disorders, caused by malfunction of the acetylcholine (AcCh) or muscarinic system, by administering a non-toxic effective amount of a compound of formula I.

18 Claims, No Drawings

1,2,3-TRIAZOLE AND TETRAZOLE SUBSTITUTED PIPERIDINE OR TETRAHYDROPYRIDINE COMPOUNDS USEFUL AS ACETYLCHOLINE AGONISTS

Matter enclosed in heavy brackets [ ] appears in the original patent but forms no part of this reissue specification; matter printed in italics indicates the additions made by reissue.

BACKGROUND OF THE INVENTION

AcCh is known to be a neurotransmitter in the peripheral as well as the central nervous system (CNS). Reduced function of AcCh in the CNS, probably as a result of degeneration of neurones utilizing AcCh as a neurotransmitter, is believed to be related to the etiology of various diseases such as Alzheimer's disease and Down's syndrome (R. M. Marchbanks, J. Neurochem. 39 (1982) 9–15; R. D. Terry and P. Davies, Ann. Rev. Neurosci., 3 (1980) 77; N. R. Sims, D. M. Bowen, S. J. Allen, C. C. T. Smith, D. Neary, D. J. Thomas and A. N. Davidson, J. Neurochem., 40 (1983) 503–509; E. Roberts, in Ann. New York Acad. Sci. (F. Marott Sinex and C. R. Merril, editors), 396 (1982) 165–178. Furthermore, senile dementia, which may be associated with aging, appears to be somehow related to decreased AcCh activity in the CNS, and similarly impaired learning and memory functions have been associated with decreased functions of the central AcCh-system (P. S. Anderson and D. Haubrich, Ann. Rep. Med Chem., 16 (1981) 51–60.

Administrations of drugs which increase the level of AcCh by blocking the enzymatic breakdown of the transmitter or directly stimulate the AcCh-receptor, AcCh-agonists, have been found to improve the cognitive malfunctions observed in patients with senile dementia of the Alzheimer type to various degrees (Christie et al., Br. J. Phych. 138 (1981) 138–146; Harbaugh et al., Neurosurgery 15 (1984) 514–518; Beller et al., Pscyhopharmacol. 87 (1985) 147–151; Schwartz and Kohlstaedt, Life Sci. 38 (1986) 1021–1028; Summers et al., N. Engl. J. Med. 315 (1986) 1241–1245. Compounds capable of activating the AcCh receptors are therefore of primary interest. However, most known AcCh agonists, including AcCh itself, contain quaternary ammonium groups and, consequently, these compounds do not penetrate the blood-brain barrier (BBB) easily after peripheral administration. As a result of this, such compounds do not reach the AcCh receptors in the CNS but activate almost exclusively the peripheral AcCh receptors, which are unrelated to the diseases mentioned above, provoking various undesired effects.

Arecoline (methyl 1-methyl-1,2,5,6-tetrahydropyridine-3-carboxylate) is an AcCh agonist, which does not contain a quatenary ammonium group. Arecoline is a tertiary amine, and arecoline is capable of penetrating the BBB after peripheral administration. The ester group of arecoline is, however, very rapidly hydrolyzed in vivo, and arecoline has very weak and frequently negligible central effects aft peripheral administration.

SUMMARY OF THE INVENTION

According to the present invention, it his now surprisingly been found that the novel compounds of Formula I have very potent AcCh agonist activity. The 5-ring heterocyclic groups can be considered as bioisosteric with the ester group in arecoline, but in contrast to the ester group they are stable towards hydrolysis. Furthermore, the new compounds readily penetrate the blood-brain barrier upon peripheral administration.

The new compounds have high affinity to central cholinergic receptors as measured by the ability of the compounds to displace tritiated oxotremorine-M from rat brain homogenates. The compounds also have high affinity to central muscarinic M-1 receptors, as defined by their ability to displace tritiated [pirenzephine] *pirenzepine* from rat brain homogenates.

The potent central activity of the compounds in vivo can be demonstrated by the ability of the compounds to induce hypothermia in mice or to prevent isoniazid induced convulsions in mice. It shall be mentioned, however, that compounds with high selectivity for M-1 receptors are without nativity in the hypothermia test. Compared with the potent central activity they show only minor peripheral side effects.

Moreover, the compounds of Formula I have very low toxicity as compared to therapeutic effective doses.

This invention also includes pharmaceutically acceptable salts of the compounds of Formula I formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylenesalicylic, methanesulfonic, ethanedisulfonic, acetic, propionic, tartaric, salicylic citric, [gluomic] *gluconic*, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

When either $R^2$ or $R^3$ is different from hydrogen, or when $R^2$ and $R^3$ are different and bound to the same carbon atom, or when $R^2$ and $R^3$ are the same and bound to the same carbon atom and the piperidine ring is saturated, the compounds of formula I can be separated into two enantiomeric forms. When either $R^2$ or $R^3$ is different from hydrogen and the piperidine ring is saturated, or when $R^2$ and $R^3$ are the same or different and bound to different carbon atoms and not being hydrogen, the compounds of formula I can be separated in cis and trans forms, each separable in two enantiomeric forms. It is understood, that the present invention encompasses all enantiomers and mixtures thereof, as well as the E- and the Z-forms and mixtures thereof.

In the present context, the term "lower alkyl" designates $C_{1-6}$ alkyl which may be straight or branched, such as methyl, ethyl, propyl isopropyl, butyl, tert. butyl, pentyl or hexyl. Preferably, the term "lower alkyl" designates $C_{1-4}$ alkyl which may be straight or branched, such as methyl, ethyl, propyl isopropyl, butyl, or tert.butyl. The term "lower alkenyl" designates a $C_2$–$C_6$ straight or branched alkyl group which contains a double bond, such as 2-propenyl, 2-butenyl, 2-pentenyl, 2-hexenyl, 2-ethyl-2-propenyl or 3-methyl-2-butenyl. The term "lower alkadienyl" designates a $C_3$–$C_6$ straight or branched alkyl group containing two double bonds, such as allenyl, 1,2-, 1,3- or 2,3-butadienyl, 1,2-, 1,3- or 2,4-pentadienyl, or 2-methyl-2,4-pentadienyl. The term "lower alkynyl" designates a $C_2$–$C_6$ straight or branched alkyl group containing a triple bond, such as 2-propynyl, 2-butynyl, 2-pentynyl, 2-hexynyl or 4methyl-2-pentynyl. Where a phenyl group is substituted with halogen, lower alkyl, or lower alkoxy, [they] *it* may be mono-, di- or tri-substituted, and when [they are] *it is* di- or tri-substituted the substituents may be the same or different. The term "lower alkoxy" designates oxy to which is attached a lower alkyl group. Preferred groups are methoxy and ethoxy. The term "halogen" designates F, Cl, Br, or I; F, Cl and Br are preferred.

Specific examples of the group "het" include oxazole, isoxazole, thiazole, isothiazole, pyrazole, imidazole, 1,2,3- and 1,2,4-triazole, 1,2,4- and 1,3,4-thiadiazole and tetrazole and, most preferably, oxazole, thiazole, 1,2,3-triazole or tetrazole.

$R^1$, $R^2$ and $R^3$ are, respectively, most preferably hydrogen or methyl, $R^4$ and $R^5$ are, respectively, most preferably hydrogen, methyl, 2-propynyl, methoxy or methylthio.

The compounds of formula I may—according to the present invention—be prepared by (a) hydrolysis or hydrogenolysis of a compound of the formula II:

II

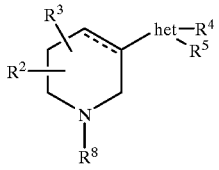

in which "het", $R^2$, $R^3$, $R^4$ and $R^5$ are as defined above, and $R^8$ is in amino-protecting group readily removable, or (b) reducing a compound of the formula III:

III

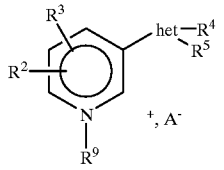

in which "het", $R^2$, $R^3$, $R^4$ and $R^5$ are as defined above, $R^9$ is defined as $R^1$ excluding hydrogen and A may be a conjugate base of an inorganic acid, with a reducing agent, or (c) treating a compound of the formula IV:

IV

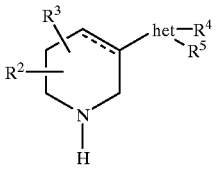

where "het", $R^2$, $R^3$, $R^4$ and $R^5$ are as defined above, with a compound of Formula V, where $R^9$ is defined as above and X is a leaving group $R^9$—X or (d) treating a compound of the formula VI:

VI

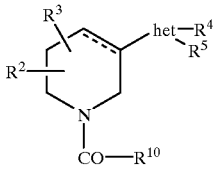

in which "het", $R^2$, $R^3$, $R^4$ and $R^5$ are as defined above, and $R^{10}$ is hydrogen, lower alkyl or lower alkoxy with a reducing agent, or (e) catalytic [hydrogenization] *hydrogenation* of compounds of formula VII or VIII:

VII

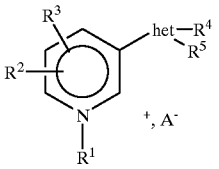

VIII

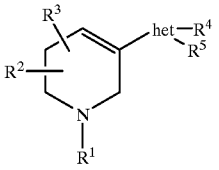

in which "het", $R^1$, $R^2$, $R^3$, $R^4$, $R^5$ and A are as defined above, or (f) treating an amide of formula IX $R^6CO—NH_2$ IX wherein $R^6$ is as defined above with formaldehyde and a compound of formula IV, or (g) by treating compounds of formula IV with a compound of formula X $R^6O—CO—X$ X wherein $R^6$ is as defined above, whereupon the compound of formula I is isolated as the free base or a pharmaceutically acceptable acid addition salt thereof and, if desired, separated in the individual stereo isomers.

Specific examples of $R^8$ in formula II are the following.

Methoxycarbonyl, ethoxycarbonyl, 2,2,2-trichloroethoxycarbonyl, propoxycarbonyl tert. butoxycarbonyl, benzyloxycarbonyl, 4-chlorobenzyloxycarbonyl, 4-methoxybenzyl, benzyl trityl, formyl or acetyl.

As examples of the conjugate base A may be mentioned chloride, bromide, iodide, and sulphate.

As examples of the leaving group X may be mentioned chloride, bromide, iodide, or the like.

In method (a) the hydrolysis is performed under acidic or basic conditions in a solvent, preferably water, ether, ethyl acetate, acetic acid or an alcohol. Preferred acids are hydrochloric acid, hydrobromic acid or trifluoroacetic acid; preferred bases include sodium or potassium hydroxide and potassium [tertbutylate] *tert-butylate*. Hydrogenation may be performed in wellknown manner at pressures ranging from 1–150 atm. at temperatures from 20°–150° C. for 1–72 hours.

In method (b) the reducing agent may be sodium borohydride, sodium cyanoborohydride, lithium aluminium hydride or the like. Reaction with metal borohydride is normally performed in an alcohol containing 0–50% of water at temperatures from −10° C. to the boiling point of the mixture. Using lithium aluminiumhydride preferred solvents are diethylether, tetrahydrofuran or a mixture of these at temperatures from 0° C. to the boiling point of the solvent. When using formic acid as a reducing agent, potassium formate, formic acid and the compound of formula III is heated to reflux for 1–6 hours.

In method (c) the reaction is preferably performed in a solvent, e.g. alcohol, dichloromethane, DMF, or a mixture of these, the solvent containing 0–50% of water in the presence of a base, e.g. metal hydroxide, quaternary amine, a metal carbonate or -alcoholate. The reaction is carried out at temperatures from 0° C. to the boiling point of the solution.

Reaction conditions for method (d) are as defined for method (b). Of particular importance is the well-known Eschweiler-Clarke methylation.

In method (e) preferred solvents are lower alcohols, water or aqueous acids or mixtures thereof. Hydrogen pressure preferably 1–150 atm. using Raney-nickel, rhodium, palladium, or platinum as catalysts. Ammonium formate may be used as hydrogen donor instead of hydrogen gas.

Preferred solvents for method (f) are water or lower alcohols.

In method (g) inert solvents as dichloromethane in the presence of a tertiary amine, e.g. triethylamine, are used.

The invention may be illustrated by the following examples, which may not be construed as limiting.

EXAMPLE 1

3-Cyano-1-methylpyridinium Iodide (2)

3-Cyanopyridine (1) (104 g, 1 mol) and methyl iodide (150 g, 1.06 mol) in acetone (500 ml) was stirred for 5 hours at room temperature. Then more methyl iodide (20 g, 0.14 mol) was added, and the reaction mixture was stirred overnight at room temperature. The mixture was filtered and the solid product was washed with acetone (100 ml) and then thoroughly with ether. After drying, 199 g (0.81 mol, 81%) of the title compound were obtained, M.P. 145°–150° C.

EXAMPLE 2

3Cyano-1-methyl-1,2,5,6-tetrahydropyridine (3)

To a solution of 2 (133 g, 0.54 mol) in methanol (1000 ml) and water (200 ml) was added sodium borohydride (41 g, 1.08 mol) in portions at temperatures below 28° C. After the addition the mixture was stirred for 1 hour at room temperature. Most of the methanol was distilled off. To the residue was added saturated ammonium chloride solution (200 ml), and the mixture was extracted three times with ether (300 ml). The combined organ phases wee washed once with water and were then extracted three times with 4M hydrochloric and (300 ml). The colored aqueous phases were kept for 1 hour at room temperature, and pH was then adjusted to 14. The mixture was extracted three times with ether (250 ml), and the combined organic phases were separated from the solid byproducts. The organic phase was washed with 4 portions of saturated sodium chloride solution (200 ml), dried over magnesium sulphate and evaporated. This yielded 17.4 g (0.143 mol, 26%) of crude oily title compound, which was sufficiently pure according to the $^1H$ NMR spectrum.

EXAMPLE 3

Ethyl 3-Cyano-1,2,5,6-tetrahydropyridine-5-carboxylate (4)

A mixture of 3 (23.9 g, 0.2 mol), ethyl chloroformate (25 g, 0.23 mol) and potassium carbonate (30 g, 0.22 mol) in 1,1,1-trichloroethane (200 ml) was refluxed to overnight.

The mixture was filtered and the organic phase was washed three times with 4M hydrochloric acid (100 ml) and then twice with saturated sodium hydrogencarbonate solution (100 ml). Drying over magnesium sulphate and evaporation of the solvent in vacuo yielded 14.8 g (0.08 mol. 41%) of oily 4, which was homogeneous according to the $^1H$ NMR spectrum.

EXAMPLE 4

5-(1-[Carboxyethyl] *Ethoxycarbonyl*-1,2,5,6-tetrahydro-3-pyridyl)-tetrazole (5)

A mixture of 4 (14.3 g, 0.079 mol), aluminium chloride (11 g, 0.083 mol) and sodium azide (23.8 g, 0.37 mol) in tetrahydrofurane was refluxed under nitrogen overnight. Cold 6M hydrochloric acid (150 ml) was added at 20° C. The mixture was extracted three times with ether (100 ml), and the combined organic phases were washed three times with saturated sodium chloride solution (50 ml). Drying over magnesium sulphate and evaporation in vacuo yielded 12.7 g of crude product, which crystallized from ethanol, yielding 8 g of 5 (0.036 mol, 45%),

M.P. 113°–116° C.

EXAMPLE 5

2-Methyl-5-(1-[carboxyethyl] *ethoxycarbonyl*-1,2,5,6-tetrahydro-3-pyridyl)-2H-tetrazole (6) and 1-Methyl-5-(1-[carboxyethyl] *ethoxycarbonyl*-1,2,5,6-tetrahydro-3-pyridyl)-1H-tetrazole (7)

A mixture of 5 (7.0 g, 0.031 mol), sodium hydroxide (1.5 g, 0.038 mol), methyl iodide (6.0 g, 0.042 mol), water (15 ml) and acetone (60 ml) was refluxed for 4 hours. The mixture was filtered, and the filtrate was evaporated in vacuo. The residue was dissolved in ether (100 ml), and the solution was washed once with water (50 ml) and then three times with saturated sodium chloride solution (50 ml). The organic phase was dried over magnesium sulphate and evaporated in vacuo leaving 8.3 g of oily product, which contained 6 and 7 in the ratio 2:1 as judged from the $^1$H NMR spectrum. The product mixture was applied to a column of silica gel. Elution with ethyl acetate-heptane (1:3) yielded 3.8 g of 6 (0.016 mol. 52%), which crystallized spontaneously, M.P. 92°–94° C. Further elution with ethyl acetate yielded 1.8 g of 7 (0.0076 mol, 24%) which crystallized spontaneously, M.P. 85°–90° C. The structural assignment of the two isomers was based on the $^1$H NMR data, since it has been shown (A. K. Sørensen and N. A. Klitgaard, Acta Chem. Scand., 26 (1972), 541–548) that the signals of the protons of the methyl groups directly attached to a nitrogen atom in the tetrazole ring occur at a higher field for the 1-isomers compared to those of the 2-isomers. The $CH_3$—N— shift for 6 was 4.3 ppm, and the $CH_3$—N— shift for 7 was 4.1 ppm.

EXAMPLE 6

2-Methyl-5(1,2,5,6-tetrahydro-3-pyridyl)-2H-tetrazole, hydrobromide (8)

A mixture of 6 (2.2 g, 0.0093 mol) and 30% hydrogen bromide in acetic acid (50 ml) was stirred for 3 day at room temperature. The yellow solution was evaporated in vacuo, and ethanol was evaporated three times (50 ml). The crystalline residue was recrystallized from ethanol. This yielded 1.5 g (0.0064 mol, 69%) of title compound, M.P. 203°–205° C. Anal. ($C_7H_{12}BrN_5$) C, H, N.

EXAMPLE 7

1-Methyl-5(1,2,5,6-tetrahydro-3-pyridyl)-2H-tetrazole, fumarate (9)

A mixture of 7 (1.8 g, 0.0076 mol) and 30% hydrogen bromide in acetic acid (30 ml) was stirred for 3 days at room temperature. The solution was then evaporated in vacuo. The residue was dissolved in water (50 ml), and the aqueous solution was extracted two times with ether (25 ml). The aqueous solution was then made basic with 28% sodium hydroxide, and was then extracted three times with dichloromethane (50 ml). The combined organic phases were washed four times with saturated sodium chloride solution (25 ml). Drying over magnesium sulphate and evaporation in vacuo yielded 0.60 g of oily compound, which was dissolved in acetone (20 ml) and treated with fumaric acid until acidic reaction. Crystalline 9 was filtered off and dryed, yielding 0.66 g (0.0023 mol, 31%), M.P. 170°–173° C. Anal. ($C_{11}H_{15}N_5O_4$) C, H, N.

EXAMPLE 8

2-Methyl-5-(1-methyl-1,2,5,6-tetrahydro-3-pyridyl) 2H-tetrazole (10)

A solution of 8 (0.70 g. 0.0028 mol) in formic acid (20 ml) and 35% formaldehyde (7 ml) was refluxed overnight. The solution was evaporated in vacuo, and the residue was taken up in ether (20 ml) and 28% sodium hydroxide (20 ml). The phases were separated, and the aqueous phase was extracted three times with dichloromethane (20 ml). The combined organic phases were washed four times with saturated sodium [chdloride] *chloride* solution (20 ml). The organic phase was dried over magnesium sulphate and evaporated in vacuo yielding 0.60 g of crude 10. Crystallization from ether-light petroleum gave 0.37 g (0.0021 mol, 74%) of title compound, M.P. 86°–87° C. Anal. ($C_8H_{13}N_5$) C, H, N.

EXAMPLE 9

2-Methyl-5-(3-pyridyl)-2H-tetrazole (12)

5-(3-pyridyl)-tetrazole (11) (J. M. McManus and R. M. Herbst, J. Am. Chem. Soc., 24 (1959) 1462–64) (10 g, 0.068 mol), sodium hydroxide (2.73 g, 0.068 mol), and methyl iodide (14.5 g, 0.1 mol) in ethanol (100 ml) was stirred at 40° C. overnight. The mixture was filtered and the filtrate was evaporated. The residue was dissolved in dichloromethane (100 ml), and the solution was washed three with water (100 ml). The organic phase wan dried over magnesium sulphate and evaporated yielding 3.21 g (0.020 mol 30%) of 12 with M.P. 108°–110° C. According to the $^1$H NMR spectrum the product contained less than 10% of the 1-isomer.

EXAMPLE 10

2-Methyl-(3-piperidyl)-2H-tetrazole, hydrochloride (13)

To a solution of 12 (1.93 g, 0.012 mol) in acetone (50 ml) was added hydrogen chloride in ether until acidic reaction. The precipitate was filtered off, dried, and dissolved in methanol (25 ml). 5% palladium on charcoal (0.6 g) was added, and the mixture was shaked overnight under 3 atm. of hydrogen pressure. The catalyst was filtered off and the filtrate was evaporated to dryness. Crystallization from ethanol yielded 0.63 g (0.0031 mol, 26%) of title product M.P. 168°–172° C. Anal. ($C_7H_{14}ClN_5$) C, H, N.

EXAMPLE 11

2-Methyl-5-methyl-3-piperidyl)-2H-tetrazole, oxalate (14)

The title compound was prepared from 13 (2.0 g, 0.0098 mol) as described in Example 8. Yield: 0.72 g (0.0026 mol, 27%), M.P. 113°–115° C. Anal. ($C_{10}H_{17}N_5O_4$) C, H. N.

EXAMPLE 12

5-(1-Methyl-3-pyridylium)-tetrazole iodide (15)

A solution of 11 (47.0 g, 0.32 mol) in N,N-dimethylformamide (250 ml) was treated with methyl iodide (90 g, 0.63 mol) at 40° C. for 2 hours. The reaction mixture was then evaporated at 60° C./1 torr, until the residue formed a thick oil. The product was crystallized from ethanol (100 ml) to yield 15 (75.3 g, 0.26 mol, 82%), M.P. 150°–155° C.

EXAMPLE 13

2-Isopropyl-5-(1-methyl-1,2,5,6-tetrahydro-3-pyridyl)-2H-tetrazole, fumarate (16)

A solution of 15 (7.6 g, 0.026 mol), sodium hydroxide (1.1 g, 0.028 mol), isopropyl iodide (6 g. 0.035 mol) and water (10 ml) in N,N-dimethylformamide (100 ml) was stirred overnight at 70° C. The mixture was filtered and the filtrate was evaporated to dryness at 60° C./1 torr. The residue was dissolved in ethanol (100 ml), and to the mixture was added sodium borohydride (5 g, 0.13 mol) in portions at less than 10° C. After the addition the mixture was stirred one hour at 10° C. and then one hour at room temperature. The clear solution was evaporated to dryness water (50 ml) was added, and the mixture was extracted three times with ether (100 ml). The combined organic phases were washed once with water (50 ml) and were then extracted three times with 4N hydrochloric acid (50 ml). The combined acidic aqueous phases were washed twice with ether (50 ml) and were then made basic with sodium hydroxide solution. The basic aqueous phase was then extracted three is with ether (100 ml), and the combined organic phases were washed with saturated sodium chloride solution until neutral reaction. The etheral phase was dried over magnesium sulphate/activated carbon and was evaporated yielding 1.0 g of an oil, which was applied to a column of silica gel which was eluted with ethyl acetate-heptane-triethylamine (45:45:10). Yield: 0.50 g of oily product, which was converted to the title fumarate. Yield; 0.67 g (0.0046 mol, 18%), M.P. 108°–110° C. Anal. ($C_4H_{21}N_5O_4$), C, H, N.

EXAMPLE 14

2-Isopropyl-5-(1,2,5,6-tetrahydro-3-pyridyl)-2H-tetrazole, hydrobromide (17)

Compound 5 (2 g, 0.0090 mol) was treated with isopropyl iodide instead of methyl iodide as described in Example 5. The product was transformed into the title compound as described in Example 6. Yield: 0.82 g (0.0030 mol, 33%). M.P. 158°–160° C. Anal. ($C_6H_{16}BrN_5$) C, H, N.

EXAMPLE 15

2-Ethyl-5-(1carboxyethyl-1,2,5,6-tetrahydro-3-pyridyl)-2H-tetrazole (18)

The title compound was prepared by treating 5 (5.97 g, 0.027 mol) with ethyl iodide instead of methyl iodide as described in Example 5. Yield: 4.14 g (0.0164 mol, 61%) as an oil.

EXAMPLE 16

2-Ethyl-5-(1,2,5,6-tetraydro-3-pyridyl)-2H-tetrazole, hydrobromide (19)

The title compound was prepared from 18 (1.5 g, 0.0060 mol) as described in Example 6. Yield: 0.91 g (0.0035 mol, 58%), M.P. 160°–162° C.). Anal. ($C_8H_{14}BrN_5$) C, H, N.

EXAMPLE 17

2-Ethyl-5-(1-methyl-1,2,5,6-tetrahydro-3-pyridyl)-2H-tetrazole, oxalate (20)

To a cooled solution of anhydrous aluminium chloride (3.85 g) and lithium aluminium hydride (0.96 g) in ether (50 ml) was dropwise added a solution of 18 (2.55 g, 0.010 mol) in tetrahydrofurane (20 ml) at less than 10° C. After the addition was completed the mixture was stirred for 2 hours at room temperature. The reaction was quenched in the cold with water and aqueous sodium hydroxide followed by filtration. The filtrate was washed twice with saturated sodium chloride solution. The organic phase was dried over magnesium sulphate and evaporated in vacuo to yield an oil, which was transformed into the crystalline oxalate. Yield: 1.3 g (0.0046 mol, 46%), M.P. 170°–172° C. Anal. ($C_{11}H_{17}N_5O_4$) C, H, N.

EXAMPLE 18

5-(1-t-Butyloxycarbonyl-1,2,5,6-tetrahydro-3-pyridyl)-1H-tetrazole (21)

A solution of 5 (2.07 g, 0.0093 mol) in 30% hydrogen bromide in acetic acid (20 ml) was left at room temperature for 3 days. The solution was evaporated in vacuo, and the residue was dissolved in water (20 ml). Potassium carbonate (13 g) and a solution of pyrocarbonic acid di-tert-butylester (3.4 g) in tetrahydrofurane (20 ml) was added, and the mixture was stirred overnight at room [temprature] *temperature*. The [mixing] *mixture* was evaporated in vacuo to half the original volume, and the reside was washed once with ethyl acetate. The aqueous phase was acidified to pH=3 with hydrochloric acid and was extracted 3 times with ethyl acetate. The combined organic phases were washed twice with saturated sodium chloride solution and dried over magnesium sulphate. Removal of solvent in vacuo yielded 1.33 g (0.0053 mol, 57%) of title compound as an oil.

EXAMPLE 19

2-(2-Propynyl)-5-(1,2,5,6-tetrahydropyridyl)-2H-tetrazole, hydrochloride (22)

To a solution of 21 (1.33 g, 0.0053 mol) in acetone (50 ml) was added triethylamine (1 ml) and propargyl bromide (2 ml). The mixture was heated to reflux for 4 hours and was then evaporated in vacuo. The residue was dissolved in ether and the solution was washed twice with saturated sodium chloride solution. The organic phase was dried over magnesium sulphate and evaporated in vacuo to yield an oil (1.19 g) which was eluted from silica gel with ethyl acetate-heptane (2:3). The product (0.63 g) was dissolved in ether (150 ml) saturated with hydrogen chloride. The mixture was stirred for 2 hours and filtered. The crystalline product was washed with ether and dried. Yield: 0.20 g (0.00088 mol, 17%), M.P. 173°–175° C. Anal. ($C_9H_{12}ClN_5$), C, H, N.

EXAMPLE 20

2-Allenyl-5-(1,2,5,6-tetrahydro-3-pyridyl)-2H-tetrazole, hydrochloride (23)

The title compound was prepared from 21 (2.7 g, 0.011 mol) as described in Example 19 using sodium hydroxide instead of triethylamine. Yield: 0.28 g (0.0012 mol, 11%), M.P. 166°–170° C. (dec.). Anal. ($C_9H_{12}ClN_5$), C, H, N.

EXAMPLE 21

5-(1-[Carboxyethyl] *ethoxycarbonyl*-3-piperidyl)-1H-tetrazole (24)

To a solution of 5 (14.9 g, 0.078 mol) in ethyl acetate (160 ml) acetic acid (25 ml) and 5% palladium on charcoal (1.25 g) were added. The mixture was shaken for 24 hours with 3.5 atm. of hydrogen pressure. The mixture was filtered and evaporated to yield the title compound as an oil (12.07 g, 80%).

EXAMPLE 22

5-(1-t-Butyloxycarbonyl-3-piperidyl)-1H-tetrazole (25)

The title compound was prepared from 24 (6.6 g, 0.0341 mol) as described in Example 18. Yield: 6.9 g (0.027 mol, 79%) as an oil.

EXAMPLE 23

2-(2-Propynyl)-5-(3-piperidyl)2H-tetrazole, hydrochloride (26)

The title compound was prepared from 25 (6.9 g, 0.027 mol) as described in Example 19. Yield: 0.92 g (0.004 mol, 15%), M.P. 162°–164° C. Anal. ($C_9H_{14}ClN_5$), C, H, N.

EXAMPLE 24

5-(1-[Carboxymethyl] *methoxycarbonyl*-6-methyl-1,2,5,6-tetrahydro-3-pyridyl)-tetrazole (28)

The title compound was prepared from 3-cyano-6-methylpyridine (27) (Plattner et al., Helv.Chem.Acta, 37 (1954) 1379–86) as described in Examples 1–5, using methyl chloroformate instead of ethyl chloroformate in Example 3. Overall yield 10%. M.P. 136°–138° C.

EXAMPLE 25

2-Methyl-5-(1-[carboxymethyl] *methoxycarbonyl*-6-methyl-1,2,5,6-tetrahydro-3-pyridyl)-2H-tetrazole (29)

The title compound was prepared from 28 (5 g, 0.023 mol) as described in Example 5. Yield: 3.8 g (0.016 mol, 70%) as an oil.

EXAMPLE 26

2-Methyl-5-(6-methyl-1,2,5,6-tetrahydro-3-pyridyl)-2H-tetrazole, hydrobromide (30)

The title compound was prepared from 29 (1.6 g, 0.0068 mol) as described in Example 6. Yield: 1.24 g (0.0048 mol, 70%), M.P. 193°–196° C. Anal. ($C_8H_{14}BrN_5$), C, H, N.

EXAMPLE 27

2-Methyl-5-(1,6-dimethyl-1,2,5,6-tetrahydro-3-pyridyl)-2H-tetrazole (31)

The title compound was prepared from 29 (2.0 g, 0.0084 mol) as described in Example 17. Yield: 0.93 g (0.0048 mol, 57%), M.P. 93°–95° C. Anal. ($C_9H_{15}N_5$), C, H, N.

EXAMPLE 28

2-Isopropyl-5-(1-[carboxymethyl] *methoxycarbonyl*-6-methyl-1,2,5,6-tetrahydro-3-pyridyl)-2H-tetrazole (32)

The title compound was prepared from 28 (5 g, 0.022 mol) as described in Example 5, using isopropyl iodide instead of methyl iodide. Yield: 3.23 g (0.012 mol, 55%) as an oil.

EXAMPLE 29

2-Isopropyl-5-(6-methyl-1,2,5,6-tetraydro-3-pyridyl)-2H-tetrazole, hydrobromide (33)

The title compound was prepared from 32 (1.62 g, 0.0061 mol) as described in Example 6. Yield: 0.83 g (0.0043 mol, 71%), M.P. 183°–185° C. Anal. ($C_{10}H_{18}BrN_5$), C, H, N.

EXAMPLE 30

2-Isopropyl-5-(1,6-dimethyl-1,2,5,6-tetrahydro-3-pyridyl)-2H-tetrazole (34)

The title compound was prepared from 32 (1.57 g, 0.0059 mol) as described in Example 17. The crude product was purified by chromatography on silica gel using ethyl acetate-heptane-triethylamine (45:45:10) as eluent. Yield: 0.68 g (0.0032 mol, 55%) as an oil. Anal. ($C_{11}H_{19}N_5$), C, H. N.

EXAMPLE 31

5-(1-t-Butyloxycarbonyl-6-methyl-1,2,5,6-tetrahydro-3-pyridyl)-tetrazole (35)

The title compound was prepared from 28 (2.9 g, 0.012 mol) as described in Example 18. Yield: 1.6 g (0.0060 mol, 50%) as an oil.

EXAMPLE 32

2-(2-Propynyl-5-(6-methyl-1,2,5,6-tetrahydro-3-pyridyl)-2H-tetrazole, hydrochloride (36)

The title compound was prepared from 35 (1.5 g, 0.0057 mol) as described in Example 19. Yield: 0.7 g (0.0030 mol, 51%), M.P. 174°–176° C. Anal. ($C_{10}H_{13}ClN_5$), C, H, N.

EXAMPLE 33

2-Methyl-5(1,4-dimethyl-1,2,5,6-tetrahydro-3-pyridyl)-2H-tetrazole, oxalate (38)

To a solution of 5-(4-methyl-3-pyridyl)-tetrazole (37, Crow et al., Aust. J. Chem., 28 (1975) 1741–54) (3.74 g, 0.023 mol) in acetone (44 ml) and water (11 ml), sodium hydroxide (1.1 g) and methyl iodide (3 ml) were added. The mixture was refluxed overnight and evaporated in vacuo. The residue was dissolved in water and the solution washed with dichloromethane. The aqueous solution was evaporated in vacuo, and the residue was dissolved in methanol (40 ml) and water (7.5 ml). Sodium is borohydride (1.08 g) was added in portions at less than 20° C. After stirring for 1.5 hours at room temperature the mixture was evaporated in vacuo, and the residue was dissolved in dichloromethane. The solution was washed 3 times with saturated sodium chloride solution, dried over magnesium sulphate and evaporated in vacuo to yield an oil, which was eluted from silica gel with ethyl acetate-heptane (3:2). Yield: 1.5 g as an oil, which was crystallized as the oxalate. Yield: 0.9 g (0.003 mol, 13%), M.P. 153°–155° C. Anal. ($C_{11}H_{19}N_5O_4$), C, H, N.

EXAMPLE 34

2-Methyl-5-(4-methyl-1,2,5,6-tetrahydro-3-pyridyl)-2H-tetrazole, 0.75 oxalate (39)

Compound 38 (6.3 g, 0.033 mol) was treated with ethyl chloroformate as described in Example 3. The product was transformed into the title compound as described in Example 6. The resulting hydrobromide was transformed to the base which was crystallized as the oxalate. Yield: 0.30 g (0.0013 mol, 5%), M.P. 212°–214° C. Anal. ($C_{9.5}H_{14.5}N_5O_3$), C, H, N.

EXAMPLE 35

N-(2-Cyanoethyl)-2-methyl-3-aminopropionitrile (41)

A solution of 2-methyl-3-aminopropionitrile (40) (Eastman Kodak Co., U.S. Pat. No. 2,659,739 (1950)) (197 g, 2.35 mol) and acrylonitrile (170 ml) in ethanol (250 ml) was refluxed overnight and then evaporated in vacuo to yield 41 (316 g, 98%) as a light oil.

EXAMPLE 36

Methyl 3-cyano-4-oxo-5-methylpiperidine-1-carboxylate (42)

To a well stirred solution of potassium tert.-butylate (270 g) in toluen (1.5 l) was slowly added 41 (316 g, 2.3 mol), and the mixture was stirred at reflux temperature for 1.5 hour. The mixture was cooled to room temperature and filtered. The wet filtercake was dissolved in 6N hydrochloric acid (2.5 l) and refluxed for 20 minutes. The mixture was cooled on an ice bath and neutralized with sodium hydroxide (pH=7, T less than 30° C.). More sodium hydroxide was added with cooling (185 g), and then methyl chloroformate (170 ml) was added at 10° C. After the addition the mixture was stirred for 1 hour at room temperature. The mixture was washed 2 times with ethyl acetate. The aqueous phase was acidified to pH=3 with concentrated hydrochloric acid and extracted 3 times with ethyl acetate. The combined extracts were washed twice with saturated sodium chloride solution, dried over magnesium sulphate and evaporated in vacuo to yield 42 (295 g, 63%) as an oil. Crystallization from ether gave [11] *42* with M.P. 65°–68° C.

EXAMPLE 37

1-[Carboxymethyl] *methoxycarbonyl*-4-chloro-3-cyano-5-methyl-1,2,5,6-tetrahydropyridine (43)

To a solution of 42 (40 g, 0.192 mol) in toluene (250 ml) was added tetrachloromethane (115 ml) and triphenyl phosphine (32 g), and the mixture was refluxed for 24 hours. More triphenyl pbosphine (32 g) was added, and reflux was continued for 48 hours, The mixture was cooled, filtered and evaporated in vacuo. Ethyl acetate was added, and the solution was left overnight at 5° C. Filtration and evaporation gave a heavy oil, which was applied to a column of silica gel. Elution with ethyl acetate-heptane (3:1) yielded 24 g (0.105 mol, 55%) of title compound as an oil.

EXAMPLE 38

1-[Carboxymethyl] *methoxycarbonyl*-3-cyano-5-methyl-1,2,5,6-tetrahydropyridine (44)

To a solution of 43 (24 g, 0.105 mol) in toluene (400 ml) was added azobisisobutyronitrile (6 g) and tri-n-butyltin hydride (90 g). The mixture was refluxed overnight and then evaporated in vacuo. Elution from a column of silica gel with ethyl acetate-heptane (1:2) gave the title compound as an oil. Yield: 10.4 g (0.0538 mol, 51%).

EXAMPLE 39

5-(1-[Carboxymethyl] *methoxycarbonyl*-5-methyl-1,2,5,6-tetrahydro-3-pyridyl)-tetrazole (45)

The title compound was prepared from 44 (10.4 g, 0.054 mol) as described in Example 4, Yield: 5.2 g (0.022 mol, 41%), M.P. 150°–152° C.

EXAMPLE 40

2-Methyl-5-(1-[carboxymethyl] *methoxycarbonyl*-5-methyl-1,2,5,6-tetrahydro-3-pyridyl)-2H-tetrazole (46)

The title compound was prepared from 45 (2.5 g, 0.011 mol) as descried in Example 5. Yield: 1.5 g (0.006 mol, 55%) as an oil.

EXAMPLE 41

2-Methyl-5-(5-methyl-1,2,5,6-tetrahydro-3-pyridyl)-2H-tetrazole, hydrobromide (47)

The title compound was prepared from 46 (0.60 g, 0.0024 mol) as described in Example 6. Yield: 0.30 g (0.0011 mol, 48%), M.P. 157°–159° C. Anal. ($C_8H_{14}BrN_5$), C, H, N.

EXAMPLE 42

2-Methyl-5-(1,5-dimethyl-1,2,5,6-tetrahydro-3-pyridyl)-2H tetrazole, oxalate (48)

The title compound was prepared from 46 (0.9 g, 0.0036 mol) as described in Example 17. Yield of crystalline oxalate: 0.24 g (0.00085 mol, 24%). M.P. 136°–139° C. Anal. ($C_{11}H_{17}N_5O_4$), C, H, N.

EXAMPLE 43

5-(1-t-Butoxycarbonyl-5-methyl-1,2,5,6-tetrahydro-3-pyridyl)-1H-tetrazole (49)

The title compound was prepared from 45 (2,7 g, 0.011 mol) as described in Example 18. Yield: 2.64 g (0.0099 mol, 90%) as an oil.

EXAMPLE 44

2-(2-Propynyl)-5-(5-methyl-1,2,5,6-tetrahydro-3-pyridyl)-2H-tetrazole hydrochloride (50)

The title compound was prepared from 49 (2.64 g, 0.0099 mol) as described in Example 19. Yield: 0.25 g (0.001 mol, 11%), M.P. 151°–152° C. Anal. ($C_{10}H_{14}ClN_5$), C, H, N.

EXAMPLE 45

3-Methyl-5-(1-methyl-1,2,5,6-tetrahydro-3-pyridyl)-isoxazole (52) and 5-Methyl-3-(1-methyl-1,2,5,6-tetrahydro-3-pyridyl)-isoxazole (53)

3-(1,3-Butadione)-pyridine (51, Mors et al., J. Am. Chem. Soc., 79 (1957) 4507–10) (7.3 g, 0.045 mol) was treated with methyl iodide as described in Example 1. The product was dissolved in ethanol (100 ml) and hydroxylammonium chloride (3 g) was added. The mixture was refluxed for 3 hours and was then cooled and sodium borohydride (7 g) was added in portions at less than 10° C. After stirring at room temperature overnight, the mixture was evaporated in vacuo. The residue was dissolved in dichloromethane, and the solution was washed twice with saturated sodium chloride solution. Drying over magnesium sulphate and evaporation in vacuo gave 6.1 g (0.034 mol, 76%) of a 1:1 mixture of 52 and 53.

EXAMPLE 46

3-Methyl-5(1,2,5,6-tetrahydro-3-pyridyl)-isoxazole, maleate (54) and 5-Methyl-3-(1,2,5,6-tetrahydro-3-pyridyl)-isoxazole, hydrochloride (55)

The crude mixture of 52 and 53 (6.1 g, 0.034 mol) was treated with ethyl chloroformate as described in Example 3, and the product mixture (4.7 g) was treated as described in Example 6. The mixture of hydrobromides was transformed into a mixture of bases (3.53 g) in the usual manner. Maleates of this mixture were crystallized form ethanol. The first crop contained pure 54 (0.73 g, 0.0026 mol), M.P. 139°–142° C. Anal. ($C_{13}H_{16}N_2H_2O_5$), C, H, N. The remaining product was transformed to the bases, and 55 was crystalline as the hydrochloride which was recrystallized twice from ethanol to give 55 still containing about 25% of 54. Yield: 0.2 g (0.001 mol), M.P. 149°–152° C. Anal. ($C_9H_{13}ClN_2O$) C, H, N.

EXAMPLE 47

Methyl nicotino-amidrazone (56)

A solution of 6.0 g (0.040 mol) of ethyl nicotinoimidate in 50 ml of dry ether was treated dropwise with a solution of 2.0 g (0.045 mol) of methyl hydrazine in 20 ml of dry ether at room temperature. After stirring for 1 h the solvent was removed in vacuo yielding 6.0 g (0.040 mol, 100%) of crude 56 as a yellow oil which was sufficiently pure.

EXAMPLE 48

1-Methyl-3-(3-pyridyl)-1,2,4-triazole (57)

To 6.0 g (0.040 mol) of 56, 9 ml (0.240 mol) of neat formic acid was slowly added at 5° C. The mixture was stirred for ½ at room temperature followed by reflux for 1 hour. After cooling the mixture was poured into aqueous $K_2CO_3$. Extraction with 3×100 ml of dichloromethane, drying of the organic phase over magnesium sulphate and evaporation in vacuo gave a yellow oil. Separation by chromatography (silica gel; eluent: methanol/ether=1/9) gave a colorless oil, 57.

Yield. 3.6 g (0.023 mol, 57%).

EXAMPLE 49

1-Methyl-3(1-methyl-1,2,5,6-tetrahydro-3-pyridyl)-1,2,4-triazole, hemifumarate (59)

A suspension of 6.3 g (0.020 mol) of the methiodide of 57 (prepared from 57 by the procedure described in Example 1) in 75 ml of methanol was cooled to −10° C., and 1.0 g (0.026 mol) of sodium borohydride was added. When the gas evolution had ceased, the mixture was stirred for 3 h at room temperature. Evaporation in vacuo give a red oil which was dissolved in 100 ml of a saturated sodium chloride solution. Extraction with 4×100 ml of dichloromethane, drying of the organic phase over magnesium sulfate, and evaporation in vacuo gave a red oil. The oil was dissolved in 50 ml of ether and stirred with charcoal. Filtration and evaporation gave the base of 59 as a colorless oil, 58. Yield: 1.6 g (0.009 mol, 45%). A 0.5 g portion of 58 was converted to the title compound. M.P. 181°–183° C. Anal. ($C_{11}H_{16}N_4O_2$) C, H, N.

EXAMPLE 50

1-Methyl-3-(1,2,5,6-tetrahydro-3-pyridyl-1,2,4-triazole, dihydrobromide (60)

The title compound was prepared form 58 (1.0 g, 0.0056 mol) by the procedure described in Examples 3 and 6. Yield: 0.21 g (0.0006 mol, 12%). M.P. 237°–239° C. Anal. ($C_8H_{14}Br_2N_4$) C, H, N.

EXAMPLE 51

1,5-Dimethyl-3-(3-pyridyl)-1,2,4-triazole (61)

To 12.0 g (0.080 mol) of 56, 9 ml (0.100 mol) of neat acetic acid anhydride was slowly added at 5° C. under stirring. The mixture was stirred for ½ h at room temperature followed by reflux for 1 h. After cooling the mixture was poured into aqueous potassium carbonate. Extraction with 3×100 ml of dichloromethane, drying of the organic phase over magnesium sulphate, and evaporation in vacuo gave a yellow oil which was applied to a silica gel column (eluent: methanol/ether=1/9) yielding a colorless solid, 61 (8.0 g, 0.046 mol, 57%).

EXAMPLE 52

1,5-Dimethyl-3-(1-methyl-1,2,5,6-tetraydro-3-pyridyl)-1,2,4-triazole, fumarate (63)

The title compound was prepared from 61 (8.0 g, 0.046 mol) by the procedure described in Example 49. Yield of free base, 62: 3.9 g (0.016 mol, 35%). A 0.8 g portion of 62 was converted to the title compound. Yield: 1.0 g (0.003 mol, 75%). M.P. 171°–173° C. Anal. ($C_{14}H_{20}N_4O_4$) C, H, N.

EXAMPLE 53

1,5Dimethyl-3-(1,2,5,6-tetrahydro-3-pyridyl)-1,2,4-triazole, dihydrobromide, dihydrate (64)

The title compound was prepared from 62 (2.8 g, 0.015 mol) by the procedures described in Examples 3 and 6. Recrystallization from methanol/ether gave 0.65 g (0.0017 mol, 12%) of 64. M.P. 254°–255° C. Anal. ($C_9H_{20}Br_2N_4O_2$) C, H, N.

EXAMPLE 54

3-Mercapto-5(3-pyridyl)-1,2,4-triazole (65)

To a solution of 19 g (0.200 mol) of thiosemicarbazide in 175 ml of dry pyridine, 29 g (0.200 mol) of nicotinoyl chloride was slowly added at 10° C. After reflux for 40 min. the reaction mixture was concentrated to half the original volume, 500 ml of water was added, and stored in the cold overnight The precipitate formed was removed by filtration, and the filtrate was evaporated in vacuo. The resulting heavy, yellow oil was dissolved in 300 ml of water, and 64 g (0.600 mol) of sodium carbonate in 400 ml of water was added. After reflux for 4 h the solution was cooled and acidified with conc. hydrochloric acid to pH=4. The formed, colorless precipitate, 65, was isolated by filtration and dried in vacuo. Yield: 35 g (0.297 mol, 98%).

EXAMPLE 55

3-Methylthio-5-(3-pyridyl)-1,2,4-triazole (66)

A solution of 20 g (0.100 mol) of 65 and 7.5 g (0.150 mol) of potassium hydroxide in 100 ml of water was mixed with a solution of 10 ml (0.160 mol) of methyl iodide in 100 ml of ether. After addition of 1 g of tetrabutylammonium hydrogen sulphate the mixture was stirred overnight at room temperature. The ether phase was separated and the aqueous phase extracted with 3×100 ml of ether. The combined organic phases were dried over magnesium sulphate. Removal of the solvent in vacuo gave a colorless solid, 66. Yield: 17.0 g (0.089 mol, 89%).

EXAMPLE 56

3-Methylthio-5-(1-methyl-1,2,5,6-tetrahydro-3-pyridyl)-1,2,4-triazole, fumarate (67)

The title compound was prepared from 66 (9.6 g, 0.050 mol) by the procedure described in Example 49. The crude product obtained was purified by chromatography (silica gel; eluent: triethylamine/methanol=1/99) giving 0.4 g (0.0019 mol. 4%) of the free base, which was converted to the title fumarate, 67. Yield: 0.37 g (0.0011 mol, 58%). M.P. 189°–191° C. Anal. ($C_{13}H_{18}N_4O_4$) C, H, N.

EXAMPLE 57

4-(3-Pyridyl)-1,2,3-triazole (68)

In a glass-coated bomb tube 6.5 g (0.063 mol) of 3-pyridyl acetylene (T. Sakamoto et al., Synthesis (1983) 312) and 8.7 g (0.075 mol) of trimethylsilyl azide were mixed and heated to 150° C. for 20 h. After cooling the mixture was poured into water. A colorless solid, 68, formed, which was isolated by filtration and dried. Yield: 4.0 g (0.028 mol, 44%).

EXAMPLE 58

2-Methyl-4-(3-pyridyl)-1,2,3,-triazole (69)

A solution of ca. 3.0 g (0.070 mol) diazomethane in ether was added dropwise to a solution of 6.0 g (0.04 mol) of 68 in 150 ml of ethanol at room temperature. The solution was stirred overnight at ambient temperature. Ca. 1 ml of acetic acid was added and the mixture was evaporated in vacuo. Water (75 ml) was added and the solution made basic with ammonia. Extraction with 3×100 ml of ether, drying of the organic phase over magnesium sulphate, and removal of the solvent in vacuo gave a brown solid which as applied to a silica gel column (eluent: ethyl acetate) giving a colorless solid, 69. Yield: 2.8 g (0.018 mol, 43%).

EXAMPLE 59

2-Methyl-4-(1-methyl-1,2,5,6-tetrahydro-3-pyridyl)-1,2,3-triazole, 1.5 fumarate (70)

The title compound was prepared from 69 (4.0 g, 0.014 mol) by the procedure described in Example 49. Yield of free base, 71: 2.5 g (0.014 mol, 100%). A 0.6 g portion (0.0034 mol) of 71 was converted to the title fumarate, 70. Yield: 0.18 g (0.0005 mol, 15%). M.P. 144°–145° C. Anal. ($C_{15}H_{20}N_4O_6$)C, H, N.

EXAMPLE 60

2-Methyl-4-(1,2,5,6-tetrahydro-3-pyridyl)-1,2,3-triazole, fumarate (72)

By the procedure described in Example 3, 1.9 g (0.011 mol) of 71 was converted to the corresponding ethyl carboxylate (yield: 1.5 g, 0.0064 mol, 58% of a colorless oil) which was dissolved in 25 ml of methanol. After addition of 1 g (0.025 mol) of sodium hydroxide and 1 ml (0.056 mol) of water, the mixture was refluxed for 24 h. After evaporation in vacuo, 20 ml of saturated sodium chloride solution was added followed by extraction with 4×20 ml of dichloromethane. Drying of the organic phase over magnesium sulphate and removal of the solvent in vacuo gave crude free base of 72 as a yellow oil, which was converted to the title fumarate, 72. Yield: 0.5 g (0.0018 mol, 28%). M.P. 126°–127 C. Anal. ($C_{12}H_{16}N_4O_4$)C, H, N.

EXAMPLE 61

N-Acetylmethyl-nicotinamide (73)

To a suspension of 40 g (0.370 mol) of aminoacetone in 500 ml of dry dichloromethane, 50 g (0.350 mol) of nicotinoyl chloride was added dropwise at room temperature under a nitrogen atmosphere. The mixture was refluxed 5 h followed by stirring overnight at room temperature. The colorless precipitate was collected by filtration and dissolved in 400 ml of water. After basification with ammonia the aqueous solution was extracted with 3×400 ml of dichloromethane. The combined organic phases were treated with charcoal and dried over magnesium sulphate. Removal of the solvent in vacuo gave a colorless solid, 73. Yield: 30.0 g (0.170 mol, 48%).

EXAMPLE 62

5-Methyl-2-(3-pyridyl)-oxazole (74)

A mixture of 20 g (0.110 mol) of 73 and 100 ml of conc. sulphuric acid was heated to 120° C. for 4 h. After cooling the mixture was poured over ice followed by basification with ammonia. Extraction with 3×400 ml of dichloromethane, drying of the combined organic phase over magnesium sulphate, and removal of the solvent in vacuo gave crude 74 as a red oil, which was sufficiently pure. Yield: 17 g (0.100 mol, 97%).

EXAMPLE 63

5-Methyl-2-(1-methyl-1,2,5,6-tetraydro-3-pyridyl)-oxazole, oxalate (75)

The title compound was prepared from 74 (9.0 g, 0.056 mol) by the procedure described in Example 49 giving 5.2 g (0.029 mol, 52%) of the crude, free base of 75. A 1.5 portion of the base was converted to the title oxalate, Yield: 1.6 g (0.006 mol, 75%). M.P 166°–167° C. Anal. ($C_{12}H_{16}H_2O_5$)C, H, N.

EXAMPLE 64

5-Methyl-2-(1,2,5,6-tetrahydro-3-pyridyl)-oxazole, fumarate (76)

The title compound was prepared from the free base of 75 (3.6 g, 0.020 mol) by the procedure described in Example 60 with the [extension] *exception* that the intermediate ethyl carboxylate was purified on a silica gel column (eluent: ether). The crude free base obtained was converted to the title fumarate, 76. Yield: 1.3 g (0.0046 mol, 23%). M.P. 139°–141° C. Anal. ($C_{13}H_{16}H_2O_5$)C, H, N.

EXAMPLE 65

N-Methoxycarbonylmethyl-nicotinamide (77)

A mixture of 50.0 g (0.400 mol) of nicotinic acid, 50.0 g (0.400 mol) of methyl glycinate hydrochloride, 90 g (0.440 mol) of dicyclohexylcarbodiimide, and 2 g of p-toluenesulfonic acid in 500 ml of dry pyridine was stirred overnight at room temperature. Filtration and evaporation in vacuo gave a heavy oil which was dissolved in 500 ml of water. After basification with ammonia the aqueous solution was extracted with 3×300 ml of dichloromethane. The organic phase was dried over magnesium sulphate, and removal of the solvent in vacuo gave crude 77 as a heavy yellow oil. Yield: 63.0 g (0.320 mol, 81%).

EXAMPLE 66

5-Methoxy-2-(3-pyridyl)-oxazole (78)

A solution of 19.0 g (0.100 mol) of 77 in 300 ml of dry chloroform was refluxed under vigorous stirring with 40 g of $P_2O_5$ for 24 h. The mixture was filtered after cooling. The filtrate was evaporated in vacuo leaving a red oil. The precipitate was dissolved in water at 0°–5° C. and the aqueous solution made basic with sodium carbonate. Extraction with 3×200 ml of dichloromethane, drying of the combined organic phases over magnesium sulphate, and removal of the solvent in vacuo gave a red oil which was combined with the above mentioned oil obtained from the chloroform phase. The oil was applied to a silica gel column (eluent; methanol/ether=1/19) giving a colorless oil, 78. Yield: 5.9 g (0.034 mol, 34%).

EXAMPLE 67

5-Methoxy-2-(1-methyl-1,2,5,6-tetrahydro-3-pyridyl)-oxazol, oxalate (80)

The title compound was prepared from 78 (5.3 g, 0.028 mol) by the procedure described in Example 49. The crude free base 79, obtained was purified on a silica gel column (eluent methanol/ether=1/9). Yield of 79: 1.2 g (0.006 mol, 22%). A 0.5 g portion of 79 was converted to the title oxalate, 80. Yield: 0.55 g (0.0019 mol, 74%). M.P. 113°–115° C. Anal. ($C_{12}H_{16}N_2O_6$)C, H, N.

EXAMPLE 68

5-Methoxy-2-(1,2,5,6-tetrahydro-3-pyridyl)-oxazole, 1.25 fumarate (81)

The title compound was prepared from 79 (5.2 g, 0.027 mol) by the procedure described in Example 60. The obtained free base was converted to the title fumarate, 81. Yield: 0.56 g (0.0031 mol, 11%). M.P. 159°–160° C. Anal. ($C_{14}H_{17}N_2N_7$)C, H, N.

EXAMPLE 69

4-Methyl-2-(3-pyridyl)-oxazole (82)

To 10 g (0.140 mol) of acetone oxime cooled to −10° C. neat nicotinoyl chloride (40 g, 0.280 mol) was added dropwise under a nitrogen atmosphere. A violent reaction occured and the mixture became quickly solid. The solid was heated to 120° C. for 3 h. After cooling the mixture was dissolved in ice water and ammonia. After addition of 300 ml of ether the mixture was treated with charcoal, filtered, and the ether phase separated. The aqueous phase was extracted with 2×200 ml of ether, and the combined organic phase dried over magnesium sulphate. Removal of solvent in vacuo gave crude 82 as a red oil. Yield: 3.9 g (0.024 mol, 17%).

EXAMPLE 70

4-Methyl-2-(1-methyl-1,2,5,6-tetrahydro-3-pyridyl)-oxazole, oxalate (84)

The title compound was prepared from 82 (5.6 g, 0.035 mol) by the procedure described in Example 49. The free base, 83, was obtained as a red oil. Yield: 2.8 g (0.016 mol, 46%). A 0.8 g portion of 83 was converted to the title oxalate. Yield: 0.7 g (0.0026 mol, 58%). M.P. 197°–199° C. Anal. ($C_{12}H_{16}N_2O_5$)C, H, N.

EXAMPLE 71

4-Methyl-2-(1,2,5,6-tetrahydro-3-pyridyl)-oxazole, fumarate (85)

The title compound was prepared from 83 (2.0 g, 0.011 mol) by the procedure described in Example 60. The free base obtained was converted to the title fumarate, 85. Yield: 0.4 g (0.0015 mol, 14%). M.P. 179°–181° C. Anal. ($C_{13}H_{16}N_2O_5$)C, H, N.

EXAMPLE 72

4,4-Dimethyl-2-(3-pyridyl)-oxazoline (86)

A solution of 69 g (0.500 mol) of methyl nicotinoate and 45 g (0.500 mol) of 2-amino-2,2,dimethyl-ethanol in 600 ml of toluene was refluxed with a water separator overnight. The solvent was removed in vacuo, 300 ml of water added, and the aqueous solution extracted with 3×300 ml of dichloromethane. Drying of the organic phase over magnesium sulphate and evaporation in vacuo gave a red oil which was filtered through silica gel (eluent: methanol/ether=1/19). Removal of solvents in vacuo gave a yellow oil, 86. Yield: 30.0 g (0.170 mol, 34%).

EXAMPLE 73

4,4-Dimethyl-2-1-methyl-1,2,5,6-tetrahydro-3-pyridyl)-oxazoline, fumarate (87)

The title compound was prepared from 86 (10.0 g, 0.051 mol) by the procedure described in Example 49. The crude product obtained was applied to a silica gel column (eluent: triethylamine/methanol/ether=1/5/44) giving 4.4 g of the free base which was converted to the title fumarate, 87. Yield: 5.4 g (0.017 mol, 30%). M.P. 156°–158° C. Anal. ($C_{15}H_{22}N_2O_5$)C, H, N.

EXAMPLE 74

5-Methyl-2-(3-pyridyl)-thiazole (88)

To a solution of 8.0 g (0.045 mol) of 73 in 125 ml of toluene, 10 g (0.045 mol) of $P_4S_{10}$ was added. The suspension was refluxed for 4 h and left at room temperature overnight. The mixture was poured into ice water followed by basification with ammonia. The two-phase system was stirred with charcoal and filtered. The toluene phase was separated and the aqueous phase extracted with 2×100 ml of toluene. The combined organic phase were dried over $MgSO_4$ and evaporated in vacuo leaving a heavy, yellow oil, 88. Yield: 2.3 g (0.013 mol), 29%).

EXAMPLE 75

5-Methyl-2-(1-methyl-1,2,5,6-tetrahydro-3-pyridyl)-thiazole, hemifumarate (90)

The title compound was prepared from 88 (2.2 g, 0.013 mol) by the procedure described in Example 49. The crude free base obtained, 89, was converted to the title fumarate, 90. Yield: 0.8 g (0.0032 mol, 25%). M.P. 159°–160° C. Anal. ($C_{12}H_{16}N_2O_2S$)C, H, N.

EXAMPLE 76

5-Methyl-2-(1,2,5,6-tetrahydro-3-pyridyl[]thiaole])-*thiazole*, fumarate (91)

The title compound was prepared from 89 (1.8 g, 0.009 mol) by the procedure described in Example 60. The free base obtained was converted to the title fumarate, 91. Yield: 1.1 g (0.0037 mol. 41%). M.P. 206°–209° C. Anal. ($C_{13}H_{16}N_2O_4S$)C, H, N.

EXAMPLE 77

5-Methylthio-2-(3-pyridyl)-thiazole (92)

A solution of 8.2 g (0.042 mol) of 77 in 250 ml of toluene was treated with 11.0 g (0.050 mol) of $P_4S_{10}$ and refluxed for 3 h. After cooling to 5° C. 100 ml of conc. ammonia was added dropwise followed by addition of 50 ml of water. The organic phase was separated and the aqueous phase extracted with 2×100 ml of toluene. The combined organic phases were dried over magnesium sulphate and evaporated in vacuo leaving a brown oil which was applied to a silica gel column (eluent: methanol/ether=1/19) yielding 0.5 g (0.0024 mol, 6%) of 92as a yellow oil.

EXAMPLE 78

5-Methylthio-2-(1-methyl-1,2,5,6-tetrahydro-3-pyridyl)-thiazole, fumarate (93)

The title compound was prepared from 92 (0.5 g, 0.0024 mol) by the procedure described in Example 49. The crude free base obtained was converted to the title fumarate, 93. Yield: 0.18 g (0.0005 mol, 21%). M.P. 154°–157° C. Anal. ($C_{14}H_{18}N_2O_4S_2$)C, H, N.

EXAMPLE 79

1,5-Dimethyl-3-(1-methyl-3-pyridinium)-pyrazole iodide (94)

To a solution of 7.0 g (0.044 mol) of 3-methyl-5-3-pyridyl)-pyrazole (V. J. Bauer et al., J. Med. Chem. 11

(1968) 981) in 90 ml of acetone and 20 ml of water was added 2.2 (0.055 mol) of sodium hydroxide and 11.7 ml (0.180 mol) of methyl iodide at 0° C. The mixture was for 2½ h, cooled to room temperature and filtered. The precipitate was washed with acetone and dried, yielding 10.9 g (0.035 mol, 80%) of 94. M.P. 230°–234° C.

EXAMPLE 80

1,5-Dimethyl-3-(1-methyl-1,2,5,6-tetrahydro-3-pyridyl)-pyrazole, dihydrochloride (95)

The title compound was pared from 94 (10.8 g, 0.034 mol) by the procedure described in Example 49. The crude free base obtained was converted to the title hydrochloride, 95. Yield: 6.4 g (0.024 mol. 71%). M.P. 218°–226° C. Anal. ($C_{11}H_{19}N_3Cl_2$)C, H, N.

The compounds of Formula I have been tested in reliable and recognize pharmacological tests which may be described as follows:

Affinity to central cholinergic receptors in vitro was measured as the ability of the compounds to displace $^3$H-oxotremorine-M (Oxo-M) from rat brain homogenates, while affinity to central muscarinic M-1-receptors in vitro was measured as the ability of the compounds to displace $^3$H-pirenzepin (Pz) from rat brain homogenates.

$^3$H-oxotremorine M binding was performed essentially as described by Birdsdall et al., 1980. Briefly, rat brains were homogenized in 100 vol (w/v) 10 mM Na,K-phosphate buffer (pH 7.4) and aliquots incubated with $^3$H-oxotremorine M (84.9 Ci/m-mol, NEN) alone or in the presence of test compound in a total volume of 1.5 ml for 40 min. at 30° C. The reaction was stopped by adding 5 ml cold buffer and filtered through Whatman GF/B filters soaked previously in 0.1% polyethylenimin (Sigma) for minimum 30 min. The filters were washed once with the same volume of buffer, transferred to scintillation vials and extracted in scintillation fluid (Pico-fluor 15, Packard) for at least two hours before counted in a liquid scintillation spectrometer (Beckman LS 1800). Non-specific binding was estimated at 10 $\mu$M atropine and all estimations made in triplicate. At least two displacement curves were made for each compound tested.

Birdsdall N. J. M., Hulme E. C., and Burgen A. S. V. (1980). "The Character of Muscarinic Receptors in Different Regions of the Rat Brain". Proc. Roy. Soc. London (Series B) 207, 1.

$^3$H-pirenzepine binding was performed essentially as described by Watson et al., 1983, the conditions being very much the same as for $^3$H-oxotremorine binding, except that aliquots were incubated with 1.0 nM $^3$H-pirenzepine for 60 min. at 25° C. and that the reaction was stopped by direct filtration followed by 3 washes with 4 ml buffer.

Watson, M., Yamamura, H. I., and Roeske, W. R. (1983). "A unique regulatory profile and regional distribution of $^3$H-pirenzepin binding in the rat provide evidence for distinct M1 and M2 muscarinic receptor subtypes". Life Sci. 32 (1983) 3001–3011.

RESULTS

| Compound | Oxo-M, $IC_{50}$($\mu$M) | Pz, $IC_{50}$($\mu$M) |
|---|---|---|
| 8 | 0.0063 | 2.1 |
| 9 | 3.2 | 27.0 |
| 10 | 0.0087 | 0.39 |
| 13 | 0.047 | 3.6 |
| 14 | 1.7 | 7.4 |
| 16 | 0.12 | 0.13 |
| 17 | 0.28 | 0.48 |
| 19 | 0.032 | 1.5 |
| 20 | 0.016 | 0.13 |
| 22 | 0.014 | 0.38 |
| 23 | 0.14 | 1.1 |
| 26 | 0.044 | 0.40 |
| 30 | 0.25 | 1.4 |
| 31 | 0.31 | 0.14 |
| 33 | 0.32 | 0.90 |
| 34 | 0.18 | 0.35 |
| 36 | 0.39 | 0.25 |
| 38 | 1.0 | 1.2 |
| 39 | 0.81 | 1.5 |
| 47 | 0.098 | 0.28 |
| 48 | 0.68 | 1.8 |
| 50 | 0.062 | 0.068 |
| 54 | 0.23 | 4.0 |
| 55 | 1.0 | 2.5 |
| 59 | 0.28 | 0.61 |
| 60 | 1.4 | 4.9 |
| 63 | 0.71 | 0.16 |
| 64 | 2.1 | 2.4 |
| 67 | 1.5 | 2.0 |
| 70 | 0.0011 | 0.0055 |
| 72 | 0.00048 | 0.79 |
| 75 | 0.057 | 0.37 |
| 76 | 0.19 | 1.3 |
| 80 | 0.097 | 1.5 |
| 81 | 0.22 | 4.2 |
| 84 | 0.028 | 0.058 |
| 85 | 0.0075 | 1.4 |
| 87 | 0.13 | 0.40 |
| 90 | 0.18 | 0.42 |
| 91 | 0.36 | 1.0 |
| 93 | 0.018 | 0.13 |
| 95 | 0.35 | 0.18 |

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection.[-Results upon administration to human beings have been very gratifying.]

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for composition containing 2-methyl-5-(1,2,5,6-tetrahydro-3-pyridyl)-2H-tetrazole, hydrobromide (Compound 8) as the active ingredient, are as follows:

| (1) Tablets containing 5 milligrams of Compound 8 calculated as the free base: | |
|---|---|
| Compound 8 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |
| (2) Tablets containing 50 milligrams of Compound 8 calculated as the free base: | |
| Compound 8 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |
| (3) Syrup containing per milliliter: | |
| Compound 8 | 10 mg |
| Sorbitol | 500 mg |
| Tragscanth | 7 mg |
| Glycerol | 50 mg |
| Methyl-paraben | 1 mg |
| Propyl-paraben | 0.1 mg |
| Ethanol | 0.005 ml |
| Water | ad 1 ml |
| (4) Solution for injection containing per milliliter: | |
| Compound 8 | 50 mg |
| Acetic acid | 17.9 mg |
| Sterile water | ad 1 ml |
| (5) Solution for injection containing per milliliter: | |
| Compound 8 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of in said addition salt the acid is preferably selected so as to contain an anion which is non-toxic and pharmacologically acceptable, at least in usual therapeutic doses. Representative salts which are included in this preferred group are the hydrochlorides, hydrobromides, sulphate, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organ solvent drying the extract and evaporating to dryness or fractionally distilling to effect isolation of the free basic amine.

We claim:

1. A novel compound of the following formula, where the dotted line designates an optional bond:

I

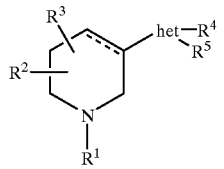

wherein

"het" designates 1,2,3-triazole or tetrazole;

$R^1$ is selected from hydrogen, lower alkyl, which may be substituted with phenyl which may be substituted with halogen, lower alkyl, or lower alkoxy, or $R^1$ *is* a group $R^6$—CO—NH—$CH_2$— or $R^6$—O—CO—, wherein $R^6$ is lower alkyl, branched or unbranched, or phenyl which may be substituted with halogen, trifluoromethyl, lower alkyl, hydroxy, lower alkoxy, or lower acyloxy;

$R^2$ and $R^3$ are the same or different, each representing hydrogen, lower alkyl, cycloalkyl (3–6 C-atoms), lower alkenyl, lower alkadienyl, lower alkynyl, which may be substituted with hydroxy, halogen or phenyl, in which the phenyl group may be substituted with halogen, trifluoromethyl, lower alkyl, hydroxy, or lower alkoxy, $R^2$ and $R^3$ may further respectively be selected from trifluoromethyl or phenyl which may be substituted with halogen, trifluoromethyl, lower alkyl, hydroxy, lower alkoxy or lower acyloxy, or $R^2$ and $R^3$ may respectively be a group $OR^7$ or $SR^7$ wherein $R^7$ is defined as $R^2$ or $R^3$ *above*, and if "het" includes 2 or more carbon atoms, $R^4$ and $R^5$ are the same or different, and each is defined as $R^2$ or $R^3$, *provided that $R^4$ and $R^5$ are not $OR^7$ or $SR^7$, bonded to nitrogen*, and if "het" includes only one carbon atom, there is only one substituent, $R^4$, on the heterocyclic ring, and $R^4$ is defined as $R^2$ or $R^3$, *provided that $R^4$ is not $OR^7$ or $SR^1$ bonded to nitrogen* as well as individual stereo isomers and pharmaceutically acceptable acid addition salts thereof.

2. A compound according to claim 1, wherein "het" designates 1,2,3-triazole or tetrazole;

$R^1$, $R^2$ and $R^3$ designate each hydrogen or methyl, and $R^4$ and $R^5$ designate each hydrogen, methyl propargyl methoxy or methylthio;

as well as individual stereo isomers and pharmaceutically acceptable acid addition salts thereof.

3. A compound according to claim 1, selected from:

2-Methyl-5-(1,2,5,6-tetrahydro-3-pyridyl)-2H-tetrazole;

2-(2-Propynyl)-5-(5-methyl-1,2,5,6-tetrahydro-3-pyridyl)-2H-tetrazole;

2-Methyl-4-(1,2,5,6-tetrahydro-3-pyridyl)-1,2,3-triazole;

2-Ethyl-5-(1-methyl-1,2,5,6-tetrahydro-3-pyridyl)-2H-tetrazole; 2-Allenyl-5-(1,2,5,6-tetrahydro-3-pyridyl)-

2H-tetrazole; 2-Methyl-4-(1-methyl-1,2,5,6-tetrahydro-3-pyridyl)-1,2,3-triazole;

well as stereo isomers and non-toxic pharmaceutically acceptable acid addition salts thereof.

4. A pharmaceutical composition in unit dosage form comprising—as an active ingredient—a compound as defined in claim 1, and one or more pharmaceutical diluents or carriers.

5. A pharmaceutical composition in unit dosage form, according to claim 4, wherein the active ingredient is present in an amount from 0.1–100 mg per unit dosage.

6. A method of treating [disorders caused by malfunction of the acetylcholine (AcCh) or muscarinic system,] *impaired memory function associated with decreased acetylcholine activity in the central nervous system* comprising the step of administering to a subject suffering from such [disorder] *impaired memory function* an effective amount of a *muscarinic receptor agonist* compound of claim 1.

7. A method of treating [disorders caused by malfunction of the acetylcholine (AcCh) or muscarinic system,] *impaired memory function associated with decreased acetylcholine activity in the central nervous system* comprising the step of administering to a subject suffering from such [a disorder] *impaired memory function* an effective amount of a *muscarinic receptor agonist* compound of claim 2.

8. A method of treating [disorders caused by malfunction of the acetylcholine (AcCh) or muscarinic system,] *impaired memory function associated with decreased acetylcholine activity in the central nervous system* comprising the step of administering to a subject suffering from such [a disorder] *impaired memory function* an effective amount of a *muscarinic receptor agonist* compound of claim 3.

9. A pharmaceutical composition in unit dosage form comprising—as an active ingredient—a compound of claim 2 and one or more pharmaceutical diluents or carriers.

10. A pharmaceutical composition in unit dosage form comprising—as an active ingredient—a compound of claim 3 and one or more pharmaceutical diluents or carriers.

11. Method of claim 6, wherein the compound is administered in an amount from 0.1 to 100 mg per unit dosage.

12. Method of claim 7, wherein the compound is administered in an amount from 0.1 to 100 mg per unit dosage.

13. Method of claim 8, wherein the compound is administered in an amount from 0.1 to 100 mg per unit dosage.

14. Composition of claim 9, in unit dosage form wherein the active ingredient is present in an amount from 0.1 to 100 mg per unit dosage.

15. Composition of claim 10, in unit dosage form wherein the active ingredient is present in an amount from 0.1 to 100 mg per unit dosage.

*16. The method of claim 6 wherein said subject suffers from Alzheimer's disease.*

*17. The method of claim 7 wherein said subject suffers from Alzheimer's disease.*

*18. The method of claim 8 wherein said subject suffers from Alzheimer's disease.*

* * * * *